US007915272B2

(12) United States Patent
Peters et al.

(10) Patent No.: US 7,915,272 B2
(45) Date of Patent: *Mar. 29, 2011

(54) 1,4-DIAZA-BICYCLO[3.2.2]NONYL PYRIMIDINYL DERIVATIVE AND ITS MEDICAL USE

(75) Inventors: Dan Peters, Malmö (SE); Gunnar M. Olsen, Smørum (DK); Elsebet Østergaard Nielsen, København K (DK); Daniel B Timmermann, Herlev (DK); Steven Charles Loechel, Frederiksberg (DK)

(73) Assignee: Neurosearch A/S, Ballerup (DK)

( * ) Notice: Subject to any disclaimer, the term of this patent is extended or adjusted under 35 U.S.C. 154(b) by 107 days.

This patent is subject to a terminal disclaimer.

(21) Appl. No.: 12/299,114

(22) PCT Filed: May 29, 2007

(86) PCT No.: PCT/EP2007/055172

§ 371 (c)(1),
(2), (4) Date: Oct. 30, 2008

(87) PCT Pub. No.: WO2007/138041

PCT Pub. Date: Dec. 6, 2007

(65) Prior Publication Data

US 2009/0270403 A1    Oct. 29, 2009

Related U.S. Application Data

(60) Provisional application No. 60/809,023, filed on May 30, 2006.

(30) Foreign Application Priority Data

May 30, 2006    (DK) ................................. 2006 00730

(51) Int. Cl.
*A61K 31/505*    (2006.01)
(52) U.S. Cl. ........................................ 514/275; 544/331
(58) Field of Classification Search .................. 514/275; 544/331
See application file for complete search history.

(56) References Cited

U.S. PATENT DOCUMENTS

| 6,407,095 | B1 | 6/2002 | Lochead et al. |
| 2004/0106603 | A1 | 6/2004 | Coe et al. |
| 2004/0127491 | A1 | 7/2004 | Peters et al. |
| 2006/0122172 | A1 | 6/2006 | Peters et al. |
| 2008/0227772 | A1 | 9/2008 | Peters et al. |
| 2008/0227773 | A1 | 9/2008 | Peters et al. |
| 2009/0181984 | A1 | 7/2009 | Peters et al. |
| 2009/0197872 | A1 | 8/2009 | Peters et al. |

FOREIGN PATENT DOCUMENTS

| FR | 2 786 770 A1 | 6/2000 |
| WO | WO-2004/016617 A1 | 2/2004 |
| WO | WO-2004/024729 A1 | 3/2004 |
| WO | WO-2004/029053 A1 | 4/2004 |
| WO | WO-2004/043960 A1 | 5/2004 |
| WO | 2005/075482 A1 | 8/2005 |
| WO | WO-2005/074940 A1 | 8/2005 |
| WO | WO-2005/075482 A1 | 8/2005 |
| WO | 2007/138039 A1 | 12/2007 |
| WO | 2007/138040 A1 | 12/2007 |
| WO | 2009/024515 A1 | 2/2009 |
| WO | 2009/024517 A1 | 2/2009 |

OTHER PUBLICATIONS

International Preliminary Report on Patentability and Written Opinion of the International Searching Authority dated Apr. 8, 2008 for International Application No. PCT/EP2008/065435 (Forms PCT/IB/273 and PCT/ISA/237).
International Preliminary Report on Patentability and Written Opinion of the International Searching Authority dated Dec. 3, 2008 for International Application No. PCT/EP2007/055170 (Forms PCT/IB/373 and PCT/ISA/237).
International Preliminary Report on Patentability and Written Opinion of the International Searching Authority dated Dec. 3, 2008 for International Application No. PCT/EP2007/055171 (Forms PCT/IB/373 and PCT/ISA/237).
International Search Report dated Jul. 30, 2007 for International Application No. PCT/EP2007/055170 (Form PCT/ISA/210).
International Search Report dated Mar. 11, 2009 for International Application No. PCT/EP2008/065435 (Form PCT/ISA/210).
International Search Report dated Sep. 10, 2007 for International Application No. PCT/EP2007/055171 (Form PCT/ISA/210).

*Primary Examiner* — James O Wilson
*Assistant Examiner* — Douglas M Willis
(74) *Attorney, Agent, or Firm* — Birch, Stewart, Kolasch & Birch, LLP

(57) ABSTRACT

This invention relates to a novel 1,4-diaza-bicyclo[3.2.2] nonyl pyrimidinyl derivative and its use in the manufacture of pharmaceutical compositions. The compound of the invention is found to be a cholinergic ligand at the nicotinic acetylcholine receptors.

Due to its pharmacological profile the compound of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

3 Claims, No Drawings

US 7,915,272 B2

1,4-DIAZA-BICYCLO[3.2.2]NONYL PYRIMIDINYL DERIVATIVE AND ITS MEDICAL USE

This application is the National Phase of PCT/EP2007/055172 filed on May 29, 2007, which claims priority under 35 U.S.C. 119(e) to U.S. Provisional Application No. 60/809,023 filed on May 30, 2006 and under 35 U.S.C. 119(a) to Patent Application No. PA 2006 00730 filed in Denmark on May 30, 2006. All of which are hereby expressly incorporated by reference into the present application.

TECHNICAL FIELD

This invention relates to a novel 1,4-diaza-bicyclo[3.2.2] nonyl pyrimidinyl derivative and its use in the manufacture of pharmaceutical compositions. The compound of the invention is found to be a cholinergic ligand at the nicotinic acetylcholine receptors.

Due to its pharmacological profile the compound of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

BACKGROUND ART

The endogenous cholinergic neurotransmitter, acetylcholine, exert its biological effect via two types of cholinergic receptors, the muscarinic Acetyl Choline Receptors (mAChR) and the nicotinic Acetyl Choline Receptors (nAChR).

As it is well established that muscarinic acetylcholine receptors dominate quantitatively over nicotinic acetylcholine receptors in the brain area important to memory and cognition, and much research aimed at the development of agents for the treatment of memory related disorders have focused on the synthesis of muscarinic acetylcholine receptor modulators.

Recently, however, an interest in the development of nAChR modulators has emerged. Several diseases are associated with degeneration of the cholinergic system i.e. senile dementia of the Alzheimer type, vascular dementia and cognitive impairment due to the organic brain damage disease related directly to alcoholism. Indeed several CNS disorders can be attributed to a cholinergic deficiency, a dopaminergic deficiency, an adrenergic deficiency or a serotonergic deficiency.

WO 2005/074940 describes diazabicyclononyl phenyl-, pyridinyl-, pyridazinyl- and thiadiazolyl-derivatives useful as modulators of the nicotinic receptors. However, the diazabicyclononyl pyrimidinyl derivative of the present invention has never been disclosed.

SUMMARY OF THE INVENTION

The present invention is devoted to the provision novel modulators of the nicotinic receptors, which modulators are useful for the treatment of diseases or disorders related to the cholinergic receptors, and in particular the nicotinic acetylcholine receptor (nAChR).

Due to its pharmacological profile the compound of the invention may be useful for the treatment of diseases or disorders as diverse as those related to the cholinergic system of the central nervous system (CNS), the peripheral nervous system (PNS), diseases or disorders related to smooth muscle contraction, endocrine diseases or disorders, diseases or disorders related to neuro-degeneration, diseases or disorders related to inflammation, pain, and withdrawal symptoms caused by the termination of abuse of chemical substances.

The compound of the invention may also be useful as diagnostic tools or monitoring agents in various diagnostic methods, and in particular for in vivo receptor imaging (neuroimaging), and they may be used in labelled or unlabelled form.

In its first aspect the invention provides a novel 1,4-diaza-bicyclo[3.2.2]nonyl pyrimidinyl which is N-[2-(1,4-diaza-bicyclo[3.2.2]non-4-yl)-pyrimidin-5-yl]-2-fluoro-benzamide;

or a pharmaceutically acceptable salt thereof.

In its second aspect the invention provides pharmaceutical compositions comprising a therapeutically effective amount of the 1,4-diaza-bicyclo[3.2.2]nonyl pyrimidinyl derivative of the invention, or a pharmaceutically-acceptable addition salt thereof, or a prodrug thereof, together with at least one pharmaceutically-acceptable carrier or diluent.

In a further aspect the invention relates to the use of the 1,4-diaza-bicyclo[3.2.2]nonyl pyrimidinyl derivative of the invention, or a pharmaceutically-acceptable addition salt thereof, for the manufacture of a pharmaceutical composition/medicament for the treatment, prevention or alleviation of a disease or a disorder or a condition of a mammal, including a human, which disease, disorder or condition is responsive to modulation of cholinergic receptors.

In a final aspect the invention provides methods of treatment, prevention or alleviation of diseases, disorders or conditions of a living animal body, including a human, which disorder, disease or condition is responsive to modulation of cholinergic receptors, which method comprises the step of administering to such a living animal body in need thereof a therapeutically effective amount of the 1,4-diaza-bicyclo [3.2.2]nonyl pyrimidinyl derivative of the invention.

Other objects of the invention will be apparent to the person skilled in the art from the following detailed description and examples.

DETAILED DISCLOSURE OF THE INVENTION

The 1,4-Diaza-bicyclo[3.2.2]nonyl Pyrimidinyl Derivative

In a first aspect a novel 1,4-diaza-bicyclo[3.2.2]nonyl pyrimidinyl derivative is provided. The 1,4-diaza-bicyclo[3.2.2] nonyl pyrimidinyl derivative of the invention is N-[2-(1,4-diaza-bicyclo[3.2.2]non-4-yl)-pyrimidin-5-yl]-2-fluoro-benzamide;

or a pharmaceutically acceptable salt thereof.

In a more preferred embodiment the 1,4-diaza-bicyclo [3.2.2]nonyl pyrimidinyl derivative of the invention is N-[2-(1,4-diaza-bicyclo[3.2.2]non-4-yl)-pyrimidin-5-yl]-2-fluoro-benzamide hydrochloric acid salt;

or a pharmaceutically acceptable salt thereof.

Pharmaceutically Acceptable Salts

The 1,4-diaza-bicyclo[3.2.2]nonyl pyrimidinyl derivative of the invention may be provided in any form suitable for the intended administration. Suitable forms include pharmaceutically (i.e. physiologically) acceptable salts, and pre- or prodrug forms of the compound of the invention.

Examples of pharmaceutically acceptable addition salts include, without limitation, the non-toxic inorganic and organic acid addition salts such as the hydrochloride derived from hydrochloric acid, the hydrobromide derived from hydrobromic acid, the nitrate derived from nitric acid, the perchlorate derived from perchloric acid, the phosphate derived from phosphoric acid, the sulphate derived from sulphuric acid, the formate derived from formic acid, the acetate derived from acetic acid, the aconate derived from aconitic acid, the ascorbate derived from ascorbic acid, the benzenesulphonate derived from benzenesulphonic acid, the benzoate derived from benzoic acid, the cinnamate derived from cinnamic acid, the citrate derived from citric acid, the embonate derived from embonic acid, the enantate derived from enanthic acid, the fumarate derived from fumaric acid, the glutamate derived from glutamic acid, the glycolate derived from glycolic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the phthalate derived from phthalic acid, the salicylate derived from salicylic acid, the sorbate derived from sorbic acid, the stearate derived from stearic acid, the succinate derived from succinic acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a compound of the invention and its pharmaceutically acceptable acid addition salt.

Examples of pharmaceutically acceptable cationic salts of a 1,4-diaza-bicyclo[3.2.2]nonyl pyrimidinyl derivative of the invention include, without limitation, the sodium, the potassium, the calcium, the magnesium, the zinc, the aluminium, the lithium, the choline, the lysine, and the ammonium salt, and the like, of a compound of the invention containing an anionic group. Such cationic salts may be formed by procedures well known and described in the art.

Additional examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a 1,4-diaza-bicyclo[3.2.2]nonyl pyrimidinyl derivative of the invention include alkali metal salts, such as the sodium salt of a compound of the invention containing a carboxy group.

The Labelled Compound

The compound of the invention may be used in its labelled or unlabelled form. In the context of this invention the labelled compound has one or more atoms replaced by an atom having an atomic mass or mass number different from the atomic mass or mass number usually found in nature. The labelling will allow easy quantitative detection of said compound.

The labelled compound of the invention may be useful as diagnostic tools, radio tracers, or monitoring agents in various diagnostic methods, and for in vivo receptor imaging.

The labelled isomer of the invention preferably contains at least one radio-nuclide as a label. Positron emitting radionuclides are all candidates for usage. In the context of this invention the radionuclide is preferably selected from $^2$H (deuterium), $^3$H (tritium), $^{13}$C, $^{14}$C, $^{131}$I, $^{125}$I, $^{123}$I, and $^{18}$F.

The physical method for detecting the labelled isomer of the present invention may be selected from Position Emission Tomography (PET), Single Photon Imaging Computed Tomography (SPECT), Magnetic Resonance Spectroscopy (MRS), Magnetic Resonance Imaging (MRI), and Computed Axial X-ray Tomography (CAT), and combinations thereof.

Methods of Producing the 1,4-Diaza-bicyclo[3.2.2]nonyl Pyrimidinyl Derivative

The 1,4-diaza-bicyclo[3.2.2]nonyl pyrimidinyl derivative of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

The present invention is devoted to the provision a novel ligand and modulator of the nicotinic receptors, which ligand and modulator is useful for the treatment of diseases or disorders related to the cholinergic receptors, and in particular the nicotinic acetylcholine receptor (nAChR). The compound of the invention shows a pronounced nicotinic acetylcholine α7 receptor subtype selectivity.

Due to its pharmacological profile the compound of the invention may be useful for the treatment of diseases or conditions as diverse as CNS related diseases, PNS related diseases, diseases related to smooth muscle contraction, endocrine disorders, diseases related to neuro-degeneration, diseases related to inflammation, pain, and withdrawal symptoms caused by the termination of abuse of chemical substances.

In a preferred embodiment the compound of the present invention may be useful for the treatment, prevention or alleviation of a cognitive disorder, learning deficit, memory deficits and dysfunction, Down's syndrome, Alzheimer's disease, attention deficit, attention deficit hyperactivity disorder (ADHD), Tourette's syndrome, psychosis, depression, Bipolar Disorder, mania, manic depression, schizophrenia, cognitive or attention deficits related to schizophrenia, obsessive compulsive disorders (OCD), panic disorders, eating disorders such as anorexia nervosa, bulimia and obesity, narcolepsy, nociception, AIDS-dementia, senile dementia, autism, Parkinson's disease, Huntington's disease, Amyotrophic Lateral Sclerosis, anxiety, non-OCD anxiety disorders, convulsive disorders, epilepsy, neurodegenerative disorders, transient anoxia, induced neuro-degeneration, neuropathy, diabetic neuropathy, periferic dyslexia, tardive dyskinesia, hyperkinesia, mild pain, moderate or severe pain, pain of acute, chronic or recurrent character, pain caused by migraine, postoperative pain, phantom limb pain, inflammatory pain, neuropathic pain, chronic headache, central pain, pain related to diabetic neuropathy, to post therapeutic neuralgia, or to peripheral nerve injury, bulimia, post-traumatic syndrome, social phobia, sleeping disorders, pseudodementia, Ganser's syndrome, pre-menstrual syndrome, late luteal phase syndrome, fibromyalgia, chronic fatigue syndrome, mutism, trichotillomania, jet-lag, arrhythmias, smooth muscle contractions, angina pectoris, premature labour, diarrhoea, asthma, tardive dyskinesia, hyperkinesia, premature ejaculation, erectile difficulty, hypertension, inflammatory disorders, inflammatory skin disorders, acne, rosacea, Chron's disease, inflammatory bowel disease, ulcerative colitis, diarrhoea, or withdrawal symptoms caused by termination of use of addictive substances, including nicotine containing products such as tobacco, opioids such as heroin, cocaine and morphine, benzodiazepines and benzodiazepine-like drugs, and alcohol.

In a more preferred embodiment the compound of the invention may be useful for the treatment, prevention or alleviation of pain, mild or moderate or severe pain, pain of acute, chronic or recurrent character, pain caused by migraine, post-operative pain, phantom limb pain, inflammatory pain, neuropathic pain, chronic headache, central pain, pain related to diabetic neuropathy, to post therapeutic neuralgia, or to peripheral nerve injury.

In an even more preferred embodiment the compound of the invention may be useful for the treatment, prevention or alleviation of diseases, disorders or conditions associated with smooth muscle contractions, convulsive disorders, angina pectoris, premature labour, convulsions, diarrhoea, asthma, epilepsy, tardive dyskinesia, hyperkinesia, premature ejaculation, or erectile difficulty.

In a still more preferred embodiment the compound of the invention may be useful for the treatment, prevention or alleviation of a neurodegenerative disorder, transient anoxia, or induced neuro-degeneration.

In a yet more preferred embodiment the compound of the invention may be useful for the treatment, prevention or alleviation of an inflammatory disorder, inflammatory skin disorder, acne, rosacea, Chron's disease, inflammatory bowel disease, ulcerative colitis, or diarrhoea.

In a further preferred embodiment the compound of the invention may be useful for the treatment, prevention or alleviation of diabetic neuropathy, schizophrenia, cognitive or attentional deficits related to schizophrenia, or depression.

Finally, the compound of the invention may be useful for the treatment of withdrawal symptoms caused by termination of use of addictive substances. Such addictive substances include nicotine containing products such as tobacco, opioids such as heroin, cocaine and morphine, benzodiazepines, benzodiazepine-like drugs, and alcohol. Withdrawal from addictive substances is in general a traumatic experience characterised by anxiety and frustration, anger, anxiety, difficulties in concentrating, restlessness, decreased heart rate and increased appetite and weight gain.

In this context "treatment" covers treatment, prevention, prophylactics and alleviation of withdrawal symptoms and abstinence as well as treatment resulting in a voluntary diminished intake of the addictive substance.

In another aspect, the compound of the invention is used as diagnostic agents, e.g. for the identification and localisation of nicotinic receptors in various tissues.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

Pharmaceutical Compositions

In another aspect the invention provides novel pharmaceutical compositions comprising a therapeutically effective amount of the 1,4-diaza-bicyclo[3.2.2]nonyl pyrimidinyl derivative of the invention.

While the compound of the invention for use in therapy may be administered in the form of the raw compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the 1,4-diaza-bicyclo[3.2.2]nonyl pyrimidinyl derivative of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by any skilled person by use of standard methods and conventional techniques appropriate to the desired formulation. When desired, compositions adapted to give sustained release of the active ingredient may be employed.

Pharmaceutical compositions of the invention may be those suitable for oral, rectal, bronchial, nasal, pulmonal, topical (including buccal and sub-lingual), transdermal, vaginal or parenteral (including cutaneous, subcutaneous, intramuscular, intraperitoneal, intravenous, intraarterial, intracerebral, intraocular injection or infusion) administration, or those in a form suitable for administration by inhalation or insufflation, including powders and liquid aerosol administration, or by sustained release systems. Suitable examples of sustained release systems include semipermeable matrices of solid hydrophobic polymers containing the compound of the invention, which matrices may be in form of shaped articles, e.g. films or microcapsules.

The 1,4-diaza-bicyclo[3.2.2]nonyl pyrimidinyl derivative of the invention, together with a conventional adjuvant, carrier, or diluent, may thus be placed into the form of pharmaceutical compositions and unit dosages thereof. Such forms include solids, and in particular tablets, filled capsules, powder and pellet forms, and liquids, in particular aqueous or non-aqueous solutions, suspensions, emulsions, elixirs, and capsules filled with the same, all for oral use, suppositories for rectal administration, and sterile injectable solutions for parenteral use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

The 1,4-diaza-bicyclo[3.2.2]nonyl pyrimidinyl derivative of the present invention can be administered in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from a 1,4-diaza-bicyclo[3.2.2]nonyl pyrimidinyl derivative of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid, which is in a mixture with the finely divided active component.

In tablets, the active component is mixed with the carrier having the necessary binding capacity in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as a mixture of fatty acid glyceride or cocoa butter, is first melted and the active component is dispersed homogeneously therein, as by stirring. The molten homogenous mixture is then poured into convenient sized moulds, allowed to cool, and thereby to solidify.

Compositions suitable for vaginal administration may be presented as pessaries, tampons, creams, gels, pastes, foams or sprays containing in addition to the active ingredient such carriers as are known in the art to be appropriate.

Liquid preparations include solutions, suspensions, and emulsions, for example, water or water-propylene glycol solutions. For example, parenteral injection liquid preparations can be formulated as solutions in aqueous polyethylene glycol solution.

The 1,4-diaza-bicyclo[3.2.2]nonyl pyrimidinyl derivative according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The compositions may take such forms as suspensions, solutions, or emulsions in oily or aqueous vehicles, and may contain formulation agents such as suspending, stabilising and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilising and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations, intended for conversion shortly before use to liquid form preparations for oral administration. Such liquid forms include solutions, suspensions, and emulsions. In addition to the active component such preparations may comprise colorants, flavours, stabilisers, buffers, artificial and natural sweeteners, dispersants, thickeners, solubilizing agents, and the like.

For topical administration to the epidermis the 1,4-diaza-bicyclo[3.2.2]nonyl pyrimidinyl derivative of the invention may be formulated as ointments, creams or lotions, or as a transdermal patch. Ointments and creams may, for example, be formulated with an aqueous or oily base with the addition of suitable thickening and/or gelling agents. Lotions may be formulated with an aqueous or oily base and will in general also contain one or more emulsifying agents, stabilising agents, dispersing agents, suspending agents, thickening agents, or colouring agents.

Compositions suitable for topical administration in the mouth include lozenges comprising the active agent in a flavoured base, usually sucrose and acacia or tragacanth; pastilles comprising the active ingredient in an inert base such as gelatin and glycerine or sucrose and acacia; and mouthwashes comprising the active ingredient in a suitable liquid carrier.

Solutions or suspensions are applied directly to the nasal cavity by conventional means, for example with a dropper, pipette or spray. The compositions may be provided in single or multi-dose form.

Administration to the respiratory tract may also be achieved by means of an aerosol formulation in which the active ingredient is provided in a pressurised pack with a suitable propellant such as a chlorofluorocarbon (CFC) for example dichlorodifluoromethane, trichlorofluoromethane, or dichlorotetrafluoroethane, carbon dioxide, or other suitable gas. The aerosol may conveniently also contain a surfactant such as lecithin. The dose of drug may be controlled by provision of a metered valve.

Alternatively the active ingredients may be provided in the form of a dry powder, for example a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

In compositions intended for administration to the respiratory tract, including intranasal compositions, the compound will generally have a small particle size for example of the order of 5 microns or less. Such a particle size may be obtained by means known in the art, for example by micronization.

When desired, compositions adapted to give sustained release of the active ingredient may be employed.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packaged tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration and continuous infusion are preferred compositions.

Further details on techniques for formulation and administration may be found in the latest edition of *Remington's Pharmaceutical Sciences* (Maack Publishing Co., Easton, Pa.).

A therapeutically effective dose refers to that amount of active ingredient, which ameliorates the symptoms or condition. Therapeutic efficacy and toxicity, e.g. $ED_{50}$ and $LD_{50}$, may be determined by standard pharmacological procedures in cell cultures or experimental animals. The dose ratio between therapeutic and toxic effects is the therapeutic index and may be expressed by the ratio $LD_{50}/ED_{50}$. Pharmaceutical compositions exhibiting large therapeutic indexes are preferred.

The dose administered must of course be carefully adjusted to the age, weight and condition of the individual being treated, as well as the route of administration, dosage form and regimen, and the result desired, and the exact dosage should of course be determined by the practitioner.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µg/kg to about 10 mg/kg/day i.v., and from about 1 µg/kg to about 100 mg/kg/day p.o.

Methods of Therapy

The 1,4-diaza-bicyclo[3.2.2]nonyl pyrimidinyl derivative of the present invention is a valuable nicotinic receptor modulator, and therefore useful for the treatment of a range of ailments involving cholinergic dysfunction as well as a range of disorders responsive to the action of nAChR modulators.

In another aspect the invention provides a method for the treatment, prevention or alleviation of a disease or a disorder or a condition of a living animal body, including a human, which disease, disorder or condition is responsive to modulation of cholinergic receptors receptors, and which method comprises administering to such a living animal body, including a human, in need thereof an effective amount of the 1,4-diaza-bicyclo[3.2.2]nonyl pyrimidinyl derivative of the invention.

In a preferred embodiment, the disease, disorder or condition relates to the central nervous system.

The preferred medical indications contemplated according to the invention are those stated above.

It is at present contemplated that suitable dosage ranges are within 0.1 to 1000 milligrams daily, preferably 10 to 500 milligrams daily, and more preferred of from 30 to 100 milligrams daily, dependent as usual upon the exact mode of administration, form in which administered, the indication toward which the administration is directed, the subject involved, the body weight of the subject involved, and further the preference and experience of the physician or veterinarian in charge.

EXAMPLES

The invention is further illustrated with reference to the following examples, which are not intended to be in any way limiting to the scope of the invention as claimed.

Example 1

Preparatory Example

All reactions involving air sensitive reagents or intermediates were performed under nitrogen and in anhydrous solvents. Magnesium sulfate was used as drying agent in the workup-procedures and solvents were evaporated under reduced pressure.

1,4-Diazabicyclo[3.2.2]nonane

Intermediate Compound

The title compound was prepared according to *J. Med. Chem.* 1993 36 2311-2320 (and according to the slightly modified method described below).

1,4-Diazabicyclo[3.2.2]nonane

Intermediate Compound

To the solution of 1,4-diazabicyclo[3.2.2]nonan-3-one (15.8 g; 113 mmol) in absolute dioxane (130 ml) $LiAlH_4$ (4.9 g; 130 mmol) was added under argon. The mixture was refluxed for 6 h and then allowed to reach room temperature. To the reaction mixture water (5 ml in 10 ml of dioxane) was added by drops, the mixture was stirred for 0.5 hour and then filtered off via glass filter. The solvent was evaporated and the residue was distilled using Kugelrohr apparatus at 90° C. (0.1 mbar) to yield 1,4-diazabicyclo[3.2.2]nonane (11.1 g; 78%) as colourless hygroscopic material.

1,4-Diazabicyclo[3.2.2]nonan-3-one

Intermediate Compound

To the solution of 3-quinuclidinone hydrochloride (45 g; 278 mmol) in 90 ml of water hydroxylamine hydrochloride (21 g; 302 mmol) and sodium acetate ($CH_3COOH \times 3H_2O$; 83 g; 610 mmol) were added, the mixture was stirred at 70° C. for 1 hour and then cooled to 0° C. The separated crystalline material was filtered off (without washing) and dried in vacuo to yield 40.0 g of oxime.

The 3-quinuclidinone oxime (40.0 g) was added during 2 hours by small portions to preheated to 120° C. polyphosphoric acid (190 g). The temperature of the solution during the reaction was kept at 130° C. After addition of all oxime the solution was stirred for 20 minutes at the same temperature, then transferred to an enameled vessel and allowed to reach room temperature. The acidic mixture was neutralized by a solution of potassium carbonate (500 g in 300 ml of water), transferred into 2000 ml flask, diluted with 300 ml of water and extracted with chloroform (3×600 ml). The combined organic extracts were dried with sodium sulphate, the solvent evaporated and the solid residue dried up in vacuo to yield 30.0 g (77%) of the mixture of lactams.

Crystallization of the obtained mixture from 1,4-dioxane (220 ml) gave 15.8 g (40.5%) of 1,4-diazabicyclo[3.2.2] nonan-3-one as colourless large crystals with mp. 211-212° C.

N-[2-(1,4-Diaza-bicyclo[3.2.2]non-4-yl)-pyrimidin-5-yl]-2-fluoro-benzamide hydrochloric acid salt Compound 1

A mixture of 4-(5-nitro-pyrimidin-2-yl)-1,4-diaza-bicyclo[3.2.2]nonane (0.71 g, 2.41 mmol), palladium (0.25 g, 10% on activated carbon) and methanol (50 ml) was stirred under hydrogen for 10 min. The reaction-mixture of 2-(1,4-diaza-bicyclo[3.2.2]non-4-yl)-pyrimidin-5-ylamine was filtered through celite and was washed with ethanol (50 ml). The ethanolic solution of 2-(1,4-diaza-bicyclo[3.2.2]non-4-yl)-pyrimidin-5-ylamine was mixed with 2-fluorobenzoyl chloride 0.38 g, 2.41 mmol) and was stirred for 90 h at room-temperature, followed by addition of 2-fluorobenzoyl chloride (38 mg, 0.24 mmol) and stirring for 15 h. Diethyl-ether (30 ml) was added. The title product precipitated as hydrochloric acid salt. Yield 0.80 g (88%). LC-ESI-HRMS of [M+H]+ shows 342.1723 Da. Calc. 342.173013 Da, dev. −2.1 ppm.

4-(5-Nitro-pyrimidin-2-yl)-1,4-diaza-bicyclo[3.2.2]nonane free base

Intermediate Compound

A mixture of 1,4-diazabicyclo[3.2.2]nonane (0.87 g, 6.90 mmol), 2-chloro-5-nitro-pyrimidine (1.56 g, 6.27 mmol) and dioxane (75 ml) was stirred at room-temperature for 15 h. Aqueous sodium bicarbonate (20 ml, 10%) was added followed by extraction with ethylacetate (3×20 ml). The organic phase was dried and evaporated and a yellow powder was isolated. Yield 0.86 g (55%). Mp 135-139° C.

Example 2

In vitro Inhibition of $^3$H-α-Bungarotoxine Binding in Rat Brain

In this example the affinity of the 1,4-diaza-bicyclo[3.2.2]nonyl pyrimidinyl derivative of the invention for binding to α$_7$-subtype of nicotinic receptors is determined in a standard assay carried out essentially as described in e.g. WO 2006/087306.

The test value is presented as an IC$_{50}$ (the concentration of the test substance which inhibits the specific binding of $^3$H-α-bungarotoxin by 50%).

The result of this experiment is presented in Table 1 below.

TABLE 1

| Inhibition of $^3$H-α-Bungarotoxine Binding | |
|---|---|
| Compound No. | IC$_{50}$ (μM) |
| 1 | <0.1 |

The invention claimed is:

1. A 1,4-diaza-bicyclo[3.2.2]nonyl pyrimidinyl compound which is
   N-[2-(1,4-Diaza-bicyclo[3.2.2]non-4-yl)-pyrimidin-5-yl]-2-fluoro-benzamide;
   or a pharmaceutically acceptable salt thereof.

2. The 1,4-diaza-bicyclo[3.2.2]nonyl pyrimidinyl compound of claim 1, which is
   N-[2-(1,4-Diaza-bicyclo[3.2.2]non-4-yl)-pyrimidin-5-yl]-2-fluoro-benzamide hydrochloric acid salt.

3. A pharmaceutical composition comprising a therapeutically effective amount of the 1,4-diaza-bicyclo[3.2.2]nonyl pyrimidinyl compound of claim 1, or a pharmaceutically-acceptable acid addition salt thereof, together with at least one pharmaceutically-acceptable carrier or diluent.

* * * * *